US007650026B2

(12) United States Patent
Deinzer

(10) Patent No.: US 7,650,026 B2
(45) Date of Patent: Jan. 19, 2010

(54) METHOD FOR OPERATING AN X-RAY DIAGNOSTICS DEVICE

(75) Inventor: Frank Deinzer, Röthenbach (DE)

(73) Assignee: Siemens Aktiengesellschaft, Munich (DE)

( * ) Notice: Subject to any disclaimer, the term of this patent is extended or adjusted under 35 U.S.C. 154(b) by 699 days.

(21) Appl. No.: 11/366,008

(22) Filed: Mar. 1, 2006

(65) Prior Publication Data
US 2007/0053572 A1 Mar. 8, 2007

(30) Foreign Application Priority Data
Mar. 2, 2005 (DE) ........................ 10 2005 010 119

(51) Int. Cl.
G06K 9/00 (2006.01)
G06K 9/32 (2006.01)
(52) U.S. Cl. ........................ 382/131; 382/132; 382/299
(58) Field of Classification Search ................. 382/131, 382/132, 299
See application file for complete search history.

(56) References Cited

U.S. PATENT DOCUMENTS

| 6,618,468 | B2 | 9/2003 | Klotz et al. | |
| 7,447,382 | B2 * | 11/2008 | Nestares et al. | 382/299 |
| 7,492,967 | B2 * | 2/2009 | Toki et al. | 382/299 |
| 2002/0191736 | A1 | 12/2002 | Shiota | |

FOREIGN PATENT DOCUMENTS

| DE | 100 37 735 A1 | 2/2002 |
| DE | 101 19 105 A1 | 10/2002 |
| EP | 1 035 420 A1 | 9/2000 |

OTHER PUBLICATIONS

Hartley et al., "Multiple View Geometry", Jun. 1999, CVPR, 1-57.*
Capel et al., "Computer Vision Applied to Super Resolution", May 2003, IEEE Signal Processing Magazine, 75-86.*
Manjunath V. Joshi, Subhasis Chaudhuri, Rajkiran Panuganti; "Super-Resolution Imaging: Use of Zoom as a Cue"; Image and Vision Computing; Dec. 2004; pp. 1185-1196; vol. 22, Issue 14; Elsevier B.V.
Sina Farsiu, Dirk Robinson, Michael Elad, Peyman Milanfar; "Advances and Challenges in Super-Resolution"; Invited Paper; International Journal of Imaging Systems and Technology; Special Issue on High Resolution Image Reconstruction; 2004; pp. 47-57; vol. 14, No. 2, Wiley Periodicals, Inc.
Sharon Peled and Yehezkel Yeshurun; "Superresolution in MRI: Application to Human White Matter Fiber Tract Visualization by Diffusion Tensor Imaging"; Magnetic Resonance in Medicine; 2001; pp. 29-35; vol. 45; Wiley-Liss, Inc.

(Continued)

Primary Examiner—Brian P Werner
Assistant Examiner—Katrina Fujita

(57) ABSTRACT

The invention relates to a method for operating an x-ray diagnostics device having an x-ray source and an x-ray image detector, between which the distance can be adjusted, with an image sequence of low resolution images being provided with a different distance, an adjustment of the coordinates systems of the images being carried out and a high resolution image being calculated from the images. A method for generating high resolution x-ray recordings is achieved here by means of a C-arm system, a so-called C-arm superresolution image.

9 Claims, 4 Drawing Sheets

OTHER PUBLICATIONS

Michael Elad and Arie Feuer; "Super-Resolution Reconstruction of Image Sequences"; IEEE Transactions on Pattern Analysis and Machine Intelligence; Sep. 1999; pp. 817-834; vol. 21, No. 9.

Michael Elad and Arie Feuer; "Restoration of a Single Superresolution Image from Several Blurred, Noisy, and Undersampled Measured Images"; IEEE Transactions on Image Processing; Dec. 1997; pp. 1646-1658; vol. 6, No. 12.

Michael Irani and Shmuel Peleg; "Super Resolution from Image Sequences"; International Conference on Pattern Recognition; 1990; pp. 115-120.

A. Papoulis; "Generalized Sampling Expansion"; IEEE Transactions on Circuits and Systems; Nov. 1977; pp. 652-654; vol. 24, No. 11.

* cited by examiner $g_1$    $g_2$    $g_N$

METHOD FOR OPERATING AN X-RAY DIAGNOSTICS DEVICE

CROSS REFERENCE TO RELATED APPLICATIONS

This application claims priority to the German Application No. 10 2005 010 119.4, filed Mar. 2, 2005 which is incorporated by reference herein in its entirety.

FIELD OF INVENTION

The invention relates to a method for operating an x-ray diagnostics device with an x-ray source and an x-ray image detector, between which the distance (SID) can be adjusted.

BACKGROUND OF INVENTION

An x-ray diagnostics device of this type known from DE 100 37 735 A1 is shown for instance in FIG. 1, which comprises a C-arm 2 which is mounted in a rotatable manner on a stand 1, an x-ray emitter 3 and an x-ray image detector 4 being disposed on the ends of said C-arm.

Floor and/ceiling tripods can also be used instead of the stand 1 shown. The C-arm 2 can also be replaced by a so-called electronic C-arm 2, which effects an electronic coupling of the x-ray emitter 3 and the x-ray image detector 4.

The x-ray image detector 4 can be rectangular or square flat semiconductor detector, which is preferably made of amorphous silicon (aSi).

A patient support table 5 for accommodating a patient to be examined is located in the radiation path of the x-ray emitter 3.

SUMMARY OF INVENTION

High resolution images are needed in the x-ray diagnostics to form the basis of a secure and correct diagnosis. The aim here is to make the smallest details visible with the highest possible quality. In the x-ray diagnostics, influence on the image quality is possible in the first instance by means of the applied x-ray dosage. In the first instance however, the x-ray dosage influences the image noise and the contrast of an x-ray image, with, in very general terms, a high x-ray dosage resulting in a noise-free and contrast-rich image.

The use of x-ray image amplifiers (RBV) and flat panel detectors (FD) has no direct influence on the resolution of an x-ray image. It depends essentially on the pixel resolution of the detector system.

So-called zoom formats on X-arm systems are the prior art for displaying a high resolution x-ray image. These methods do not use the complete x-ray image detector for image generation, but only a smaller partial surface so that the image appears larger. This procedure is also ultimately restricted however in terms of the available resolution of the RBV or FD and is not able to display anatomical details which are smaller than the physical resolution capability of the x-ray image detector. Image interpolation methods which extrapolate individual images, e.g. per bi-cubic interpolation, onto a higher resolution, are not able to process small and thus non-visible details.

With RBV and FD systems, the sole solution for improving the resolution capability is an expensive modification of the x-ray image detectors. In other words, a better x-ray image detector must offer 2048×2048 pixels on the same area instead of the 1024×1024 pixels. On the one hand this makes great demands on the detector manufacturers, who have today already reached the limits of the current technical possibilities, not to speak of the costs involved in developing a new x-ray image detector. In addition, the surface of an individual pixel which decreases when the resolution is increased has a direct influence on the x-ray quantum yield and thus also on the noise of the x-ray image for instance.

All in all, the technical possibilities for increasing the pixel resolution are very restricted.

A similar problem also exists on other areas in which images are recorded for example with current video and photo cameras. The resolution of the photo cameras can thus not be arbitrarily technically increased. In applications in which a higher detail level is required in the images, such as for instance satellite recordings and military surveillance recordings, methods have been known for some time, under the term "superresolution", which use a number of individual recordings to calculate an individual high resolution image, such as that described for instance in "Advances and Challenges in Super-Resolution" by S. Farsiu et al., Invited Paper, International Journal of Imaging Systems and Technology, Special Issue on High Resolution Image Recon struction, Vol. 14, no. 2, pp. 47-57, 2004.

Within the field of medicine, the use of a superresolution approach for generating high-resolution MRI images is only described in, "Superresolution in MRI: Application to Human White Matter Fiber Tract Visualization by Diffusion Tensor Imaging" by Sharon Peled et al., Magnetic Resonance in Medicine, 45:29-35 (2001).

The functional principle of superresolution approaches is based on an image sequence being available as an input, said image sequence consisting of a number of images which can be carried over into one another by means of an affine transformation. With satellite recordings or video sequences recorded using a video camera, this affine transformation is produced for instance by a displacement of the scenes in the image. This translation sufficiently fulfills the requirements of an affine transformation and is very easy to implement.

The general model of superresolution can be described according to M. Elad et al., "Superresolution reconstruction of an image", IEEE Transactions on Pattern Analysis and Machine Intelligence, 21:817-834, 1999 as follows: Low resolution images $g_i$ of an image sequence are the result of a projection P of a high resolution image f on their image level and an adaptation of their coordinate systems by an affine 2D transformation. Only the low resolution images can be observed, the high resolution image can not be observed due to the restricted possibilities of the camera. It thus follows that, as a result of the affine transformation, the images $g_i$ are located in different coordinate system and must in fact be located there for the approach to work.

The principle of the superresolution is now described on the basis of FIG. 2. Each box, both large and small, represents an individual pixel. FIG. 2 shows a first image 6 of a low resolution and a second image 7 displaced in the x and y direction with a similarly low resolution, which are to be fed to a high resolution image 8 by means of transformation. The pixels are small in the high resolution image 8, and in contrast large in the low resolution images 6 and 7.

The coordinate system offset required for the superresolution is very simple to generate for satellites and video recordings:

with satellite recordings:

the satellite moves around the earth by itself. The recorded images are thus offset against each other.

with video recordings:

a suitable movement is very easily possible in a hand-operated manner.

This means that in both cases, a moved scene of low resolution images forms the initial product for a high resolution image.

An object of the invention is to design an x-ray diagnostics device and a method of the type mentioned at the outset such that a maximum recognizability of the smallest details is ensured.

The object is achieved according to the invention in that an image sequence of low resolution images is provided with a different distance, an adjustment of the coordinate system of the images is carried out and a high resolution superresolution image is calculated from the images. A method for generating high resolution x-ray recordings is achieved in this way by means of a C-arm system, so-called C-arm superresolution images.

An affine 2D transformation of the low resolution images advantageously allows a high resolution image to be calculated.

The method according to the invention can include the following steps:

Generating a series of x-ray images of a motionless object by varying the SID.

Selecting any image as a reference image.

Determining the optimum affine transformations $$T_i = \begin{pmatrix} s_i & 0 & x_i \\ 0 & s_i & y_i \\ 0 & 0 & 1 \end{pmatrix}$$

in homogeneous coordinates, comprising the scaling factor and a displacement within the image level in order to determine the parameters which map the respective image onto the reference image with the minimum number of errors.

Transferring all images into a common coordinates system by means of the calculated transformations.

Superimposing all images and calculating a superresolution image.

Images are hereby achieved, the three-dimensional 2D resolution of which is greater than in the individual images.

It has proven advantageous for the scaling factor and the displacement to be determined with sub-pixel precision.

To determine the transformation, the dissimilarity can be minimized as follows for a suitable distance measure between images:

$$T_i = \underset{T}{\operatorname{argmin}}\, d(T \otimes g_i, g_R)$$

($\otimes$ is the operator who applied the transformation T to the image $g_i$).

In this case, the distance measure between images can be determined according to the invention by forming the sum of the amounts of all pixel differences.

The ratios of the reference image to the images in the optimization can advantageously be used as an initial start value for the scaling factor.

Additional images can be provided in accordance with the invention, with a modified zoom format but with an identical distance (SID).

BRIEF DESCRIPTION OF THE DRAWINGS

The invention is described in more detail below with reference to one of the exemplary embodiments displayed in the drawing, in which.

DETAILED DESCRIPTION OF INVENTION

Figure 1:
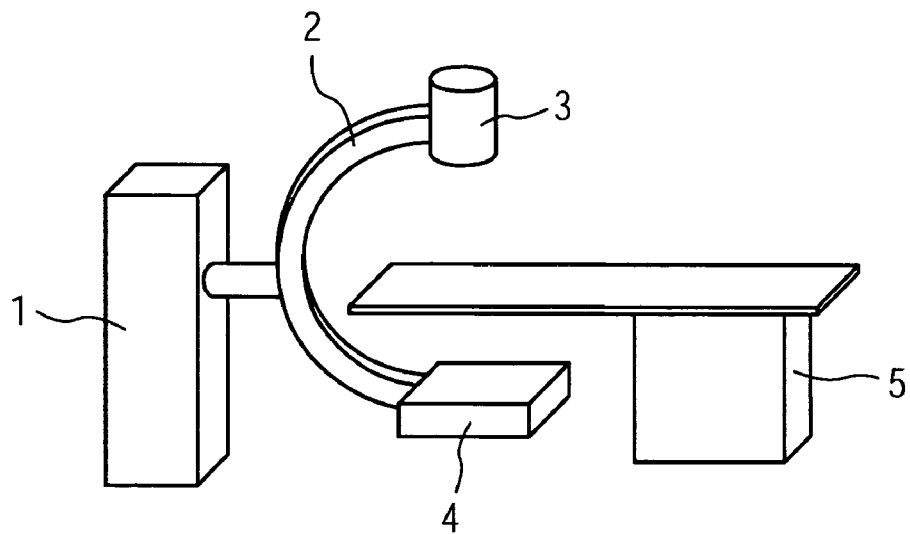
FIG. 1 shows a known x-ray diagnostics device.
Figure 2:
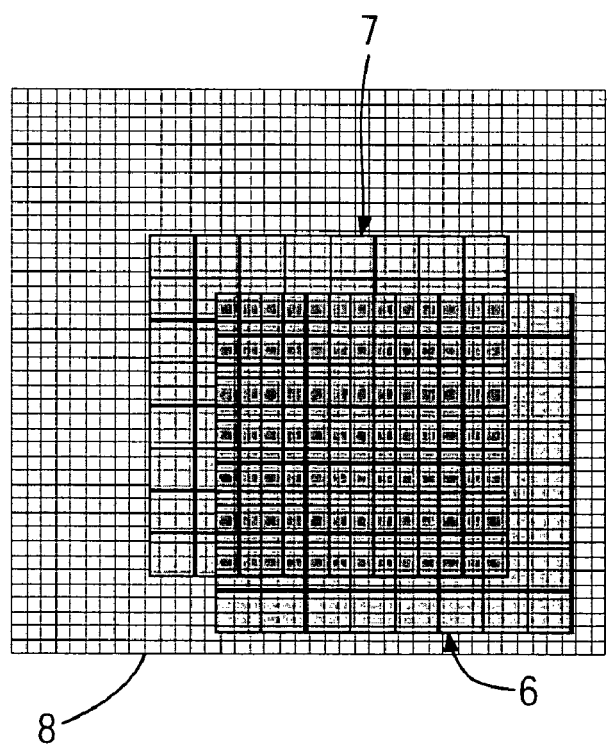
FIG. 2 shows symbolic images for describing the super-resolution.
Figure 3:
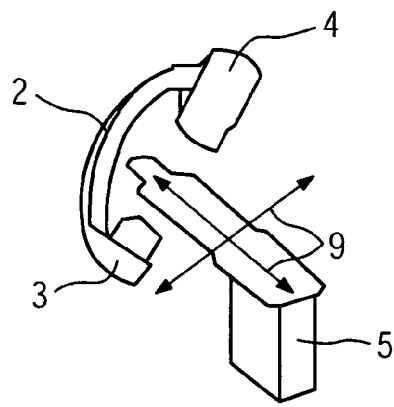
FIG. 3 shows possible movements of the patient support table

The coordinate system offset is more difficult to manage on the C-arm system, than with the previously described applications. The approach according to the invention differs from the current prior art in precisely this area. If the degrees of freedom exhibited by a C-arm system are considered, the results are as follows:

Movement of the patient support table 5 (see FIG. 3):

A patient support table 5 moved in the direction of the double arrow 9 fulfills the demands of the affine transformation in the 3D world coordinate system. A movement of this type however does not generally fulfill the 2D projection image as a result of the image production process which is described by a perspective projection. If the coordinate system offset is to be achieved by a table movement, the maximum table movement must be restricted to a few millimeters. This is however technically impractical.

Figure 4:
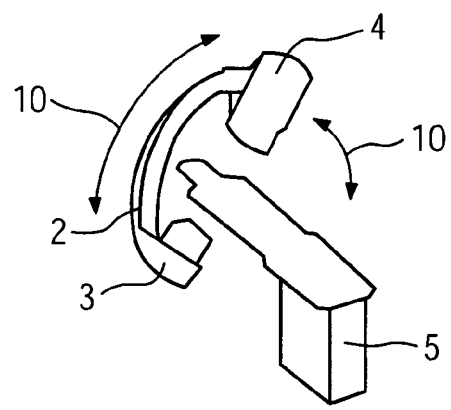
FIG. 4 shows a possible C-arm angulation.

Change in the angulation of the C-arm 2 (see FIG. 4): A C-arm angulations to be carried out in the direction of the double arrow 10 in no instances fulfills the demand for an affine transformation in the 2D x-ray projection image.

Change in the zoom format:

This is an affine transformation, but is however not suited to generating a superresolution image since only very few discrete zoom stages are available.

Figure 5:
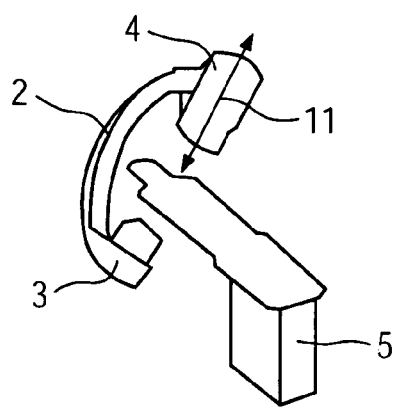
FIG. 5 shows possible modifications to the source-image distance (SID)

Change in the source image distance SID (see FIG. 5):

A C-arm system enables the x-ray image detector 4 to be operated in a motor-controlled manner in the direction of the x-ray emitter 3. The change in this distance, the SID, in the direction of the double arrow 11 involves a 2D scaling of the image and is thus an affine transformation. Additionally, it can be practically continuously varied in an adequately large area (zoom factor approximately 1.0 to 1.3.

Figure 6:
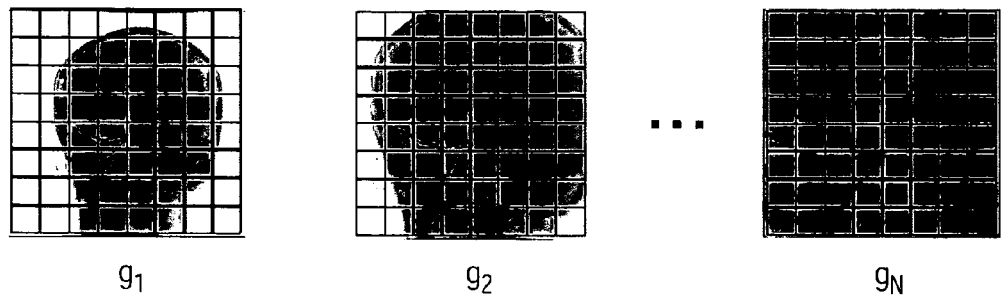
FIG. 6 shows x-ray images generated by an SID variation

This means that the change in the SID is the parameter which must be varied for a superresolution approach. An adaptation of the general theoretical superresolution requirements results in the following procedures for generating high resolution recordings:

By varying the SID, generate a series of x-ray images $g_i$ with i=1 ... N of a motionless object or a motionless patient. These images differ in terms of their scaling and are potentially displaced in relation to one another. FIG. 6 shows three x-ray images $g_1, g_2 \ldots g_N$ of this type, of different scalings, which can be combined into one high resolution x-ray image by means of the superresolution.

Select any image $g_R$ as a reference image. Determine the optimum affine transformations $T_i$, $$T_i = \begin{pmatrix} s_i & 0 & x_i \\ 0 & s_i & y_i \\ 0 & 0 & 1 \end{pmatrix} \quad (1)$$

in the homogenous coordinates and comprising the scaling factor $s_i$ a and shift ($x_i$ $y_i$) within the image level. This optimum transformation determines the parameters which map the respective image $g_i$ onto the reference image $g_R$ with the minimum number of errors. In formal terms, this means that the transformation T is sought which minimizes the dissimilarities between images (the sum of the amounts of all pixel differences for instance) for a suitable distance measure d(.,.);

$$T_i = \underset{T}{\operatorname{argmin}}\ d(T \otimes g_i, g_R) \quad (2)$$

$\otimes$ is the operator who applied the transformation T to the image $g_i$).

Finally, the affine transformation functions as a resampling of the image. It is worth noting here that $s_i$, $x_i$ and $y_i$ are to be determined with sub-pixel accuracy. After the C-arm system has provided the position of the SID for external systems, the ratios of the SID reference image $g_R$ to the SID image $g_i$ can be used in the optimization in (2) as an initial start value for $s_i$.

Naturally $g_R=g_i$ $$T_i = \begin{pmatrix} 1 & 0 & 0 \\ 0 & 1 & 0 \\ 0 & 0 & 1 \end{pmatrix}.$$

Figure 7:
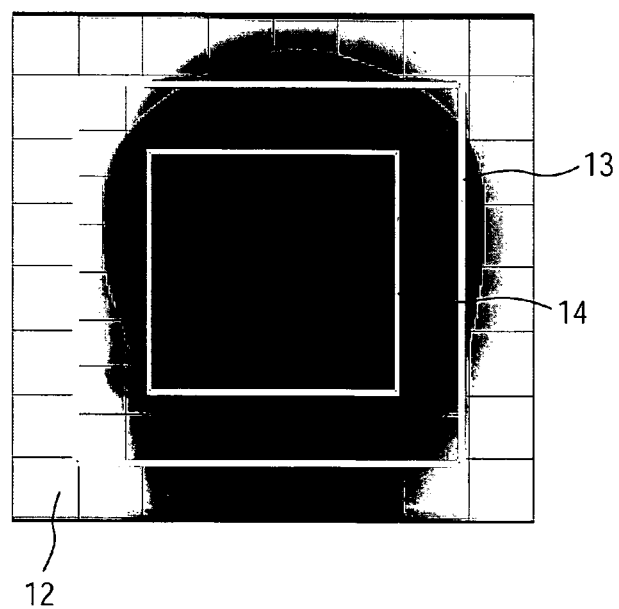
FIG. 7 shows adjustments of the coordinate systems of the x-ray images according to FIG. 6

The calculated transformations bring all images into a common coordinates system, as is show in FIG. 7. The different enlargements of the individual x-ray images result in a large x-ray image 12 with a lower resolution in an image segment (image $g_1$ corresponds to FIG. 6), an average x-ray image 13 with an average resolution and the same image center (image $g_2$ corresponds to FIG. 6) as well as a small x-ray image 14 with a high resolution (image $g_N$ corresponds to FIG. 6).

Figure 8:
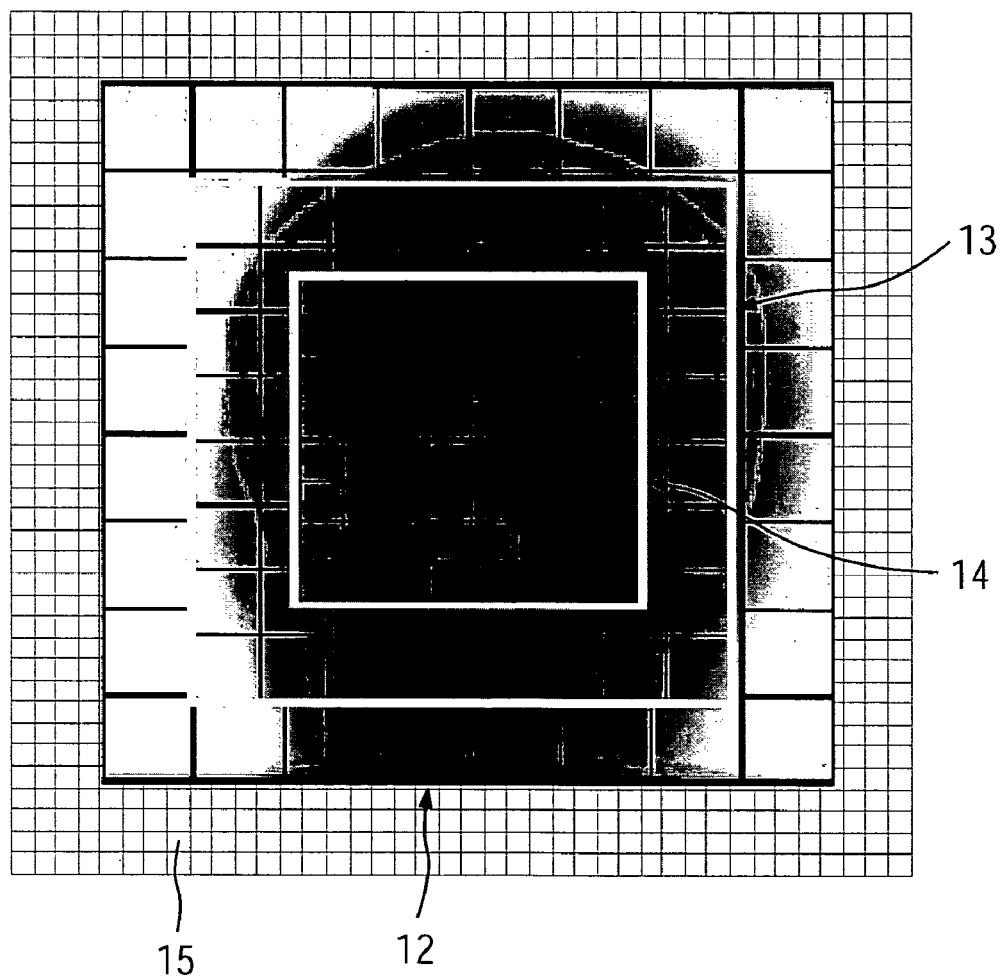
FIG. 8 shows the calculation of a superresolution image from the x-ray images according to FIG. 7.

A superresolution image 15 can be calculated, on the basis of the redundant information, from the images 12 to 14 positioned in such a way one above the other, since a number of images show the identical image segment in different resolutions, the spatial 2D resolution of said superresolution being greater than in the individual images, as can be seen in FIG. 8, on the basis of the smaller edge lengths of the individual pixels. This step is referred to as image reconstruction and is known for instance from the following works:

Generalized Sampling Theorem:

A. Papoulis. Generalized Sampling Expansion, IEEE Transactions on Circuits and Systems, vol. 24, no. 11, pp. 652-654, Nov. 1977, Iterated Backprojection:

M. Irani and S. Peleg. Superresolution from image sequences. International Conference on Pattern Recognition (ICPR 90), 115-120, 1990, Maximum Likelihood-Verfahren und das Maximum a-posteriori Propability-Verfahren [Maximum Likelihood Method and the Maximum a-posteriori Probability method]:

M. Elad and A. Feuer. Restoration of a single superresolution image from several blurred, noisy, and undersampled measured images. IEEE Transactions on Image Processing, 6(12):1646-1658, December 1997, und M. Elad and A. Feuer. Superresolution reconstruction of an image. IEEE Transactions on Pattern Analysis and Machine Intelligence, 21:817-834, 1999.

This image reconstruction allows details to be visible, which can not be recognized in an individual image. In contrast, these finenesses are visible in the superresolution image as a result of the image reconstruction and the redundant information used therefrom.

Different regions with different information content can appear with the calculation of the high-resolution x-ray image 15.

Regions which are not visible in any individual recordings 12 to 14, such as the pixel-without information in FIG. 8 for instance, which lie on the margin:

No information is available here, so that a region of this type is displayed as a homogenous single color surface, if it is to be considered.

Regions which can only be seen in an individual recording, such as the pixel with information only of the large x-ray image 12 in FIG. 8 for instance:

The resolution can naturally also be increased in these regions, without information gain. This means that no details are visible here which are not already visible in the individual recordings 12 with low resolution. Such methods for increasing resolution are a simple bi-linear interpolation for instance.

However it is worth noting that these image regions are low due to the relatively low movement region and the interest object is to some degree also centrally positioned by the treating doctor.

Regions which are visible in all individual recordings 12 to 14: The information gain in these regions is carried over fully. This means that in the part of the x-ray image 15, details are visible which were not visible in any of the individual images 12 to 14. To improve understanding, reference is made to the x-ray images of the FIGS. 6 to 8. In the individual images of FIGS. 6 and 7, the line structures are not visible in any of the low resolution x-ray images. In the high resolution superresolution image which is shown in FIG. 8, these line structures are however clear, more information is thus contained than in each individual image.

Regions which are available in some, more than 1, but not all, individual images 12 to 14;

Here, in general terms, more images are present in a region, the larger the information gain, i.e. the finally recognizable resolution improvement.

In summary, the resolution of the high resolution x-ray image 15 is always just as great and can, in principle, be selected itself. The information content, i.e., the ultimately visible structures, thus depends on how much information is available for a region, in other words in how many low resolution x-ray images 12 to 14 of the region the image was visible.

The use according to the invention of a superresolution approach provides an x-ray image quality on a C-arm system, said x-ray image quality allowing a detail level in its resolution which is nowadays not achievable using other technical possibilities. Anatomic structures or abnormal changes, which are too small for current x-ray image detectors, can be made visible.

An essential advantage is that the method according to the invention can be implemented with practically any C-arm system used nowadays.

With FD systems however, significantly better results can be expected than with former RBV systems, in which distortion correction is necessary before a superresolution approach can be used.

The invention claimed is:

1. A method for operating an x-ray diagnostics device having an x-ray source and an x-ray image detector, wherein the x-ray diagnostics device is configured to adjust a distance between the x-ray source and the x-ray image detector, the method comprising:

generating an image sequence of low resolution images, the distance set differently when recording each low resolution image and each low resolution image having a coordinate system;

assimilating the coordinate systems of the low resolution images; and calculating a high resolution image from the low resolution images using the assimilated coordinate systems.

2. The method according to claim 1, wherein the high resolution image is a super-resolution image, and assimilating the coordinate systems includes affine two-dimensional coordinate transformations of the low resolution images.

3. The method according to claim 2, wherein the image sequence is recorded from a motionless object, one of the low resolution images is selected as a reference image, the two-dimensional affine transformations include the formula $$T_i = \begin{pmatrix} s_i & 0 & x_i \\ 0 & s_i & y_i \\ 0 & 0 & 1 \end{pmatrix}$$

and are determined for each low resolution image relative to homogenous coordinates, the optimal affine transformations including a scaling factor $i_s$ and a displacement (xi, yes) within an image plane of the respective low resolution image for determining transformation parameters for mapping the respective image onto the reference image; wherein a mapping error criterion is minimized, the low resolution images are transformed to a common coordinate system using the determined two-dimensional affine transformations applied to the coordinate systems of the low resolution images, the transformed low resolution images are superimposed, and the super-resolution image is calculated from the superimposed transformed low resolution images.

4. The method according to claim 3, wherein the scaling factor and the displacement are determined with a sub-pixel precision.

5. The method according to claim 3, wherein the two-dimensional affine transformations are optimized in an iterative process, the iterative process including an initial starting value for the scaling factor determined by a ratio of the reference image relative to at least one other low resolution image.

6. The method according to claim 1, wherein the two-dimensional affine transformations minimizes a dissimilarity between a low resolution image and a transformed low resolution image, the dissimilarity described by a distance measure d, the two-dimensional affine transformations fulfilling the formula $$T_i = \operatorname*{argmin}_{T} d(T \otimes g_i, g_R),$$

wherein $\otimes$ is an operator describing a transformation T applied to image $g_i$ to generate the transformed low resolution image, and $g_r$ is a low resolution image.

7. The method according to claim 6, wherein the distance measure is determined by calculating a sum of all pixel differences relative to the low resolution and transformed low resolution images.

8. The method according to claim 1, further comprising:

generating a plurality of further low resolution images having a fixed distance but different zoom settings; and including the further low resolution images in the image sequence.

9. The method of claim 1 wherein setting of the distance differently when recording each low resolution image is effected with motor control of a C-arm to enable movement of the image detector relative to the source, thereby modifying the source image distance so that the high resolution image is a super-resolution image.

* * * * *

UNITED STATES PATENT AND TRADEMARK OFFICE
CERTIFICATE OF CORRECTION

PATENT NO. : 7,650,026 B2  Page 1 of 1
APPLICATION NO. : 11/366008
DATED : January 19, 2010
INVENTOR(S) : Frank Deinzer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 994 days.

Signed and Sealed this

Twenty-third Day of November, 2010

David J. Kappos
*Director of the United States Patent and Trademark Office*